United States Patent
Huo et al.

(10) Patent No.: US 8,426,491 B2
(45) Date of Patent: Apr. 23, 2013

(54) DENTAL COMPOSITIONS FOR COATING RESTORATIONS AND TOOTH SURFACES

(75) Inventors: Xin Huo, Dover, DE (US); Michael O'Connor, Easton, MD (US); Robert Size, York, PA (US)

(73) Assignee: DENTSPLY International Inc., York, PA (US)

( * ) Notice: Subject to any disclaimer, the term of this patent is extended or adjusted under 35 U.S.C. 154(b) by 46 days.

(21) Appl. No.: 12/151,854

(22) Filed: May 12, 2008

(65) Prior Publication Data

US 2009/0047633 A1 Feb. 19, 2009

Related U.S. Application Data

(60) Provisional application No. 60/928,766, filed on May 11, 2007.

(51) Int. Cl.
*A61K 6/08* (2006.01)
*A61C 5/00* (2006.01)

(52) U.S. Cl.
USPC ............ 523/118; 433/217.1; 433/228.1; 522/908

(58) Field of Classification Search ........... 523/118; 433/217.1, 218.1, 28.12; 106/35
See application file for complete search history.

(56) References Cited

U.S. PATENT DOCUMENTS

| | | | |
|---|---|---|---|
| 3,629,187 A * | 12/1971 | Waller | 523/115 |
| 3,905,110 A * | 9/1975 | Lee et al. | 433/216 |
| 4,503,169 A | 3/1985 | Randklev | |
| 4,936,775 A * | 6/1990 | Bennett | 433/220 |
| 5,177,120 A | 1/1993 | Hare et al. | |
| 5,318,999 A | 6/1994 | Mitra et al. | |
| 5,332,779 A | 7/1994 | Mohri et al. | |
| 5,733,949 A | 3/1998 | Imazato et al. | |
| 5,936,006 A | 8/1999 | Rheinberger | |
| 6,309,625 B1 | 10/2001 | Jensen et al. | |
| 6,355,704 B1 | 3/2002 | Nakatsuka et al. | |
| 6,399,037 B1 | 6/2002 | Pflug et al. | |
| 6,417,246 B1 | 7/2002 | Jia et al. | |
| 6,572,693 B1 | 6/2003 | Wu et al. | |
| 6,593,395 B2 | 7/2003 | Angeletakis et al. | |
| 6,693,143 B2 | 2/2004 | Pflug | |
| 6,730,715 B2 | 5/2004 | Jia | |
| 6,797,767 B2 | 9/2004 | Stannard et al. | |
| 6,818,679 B2 | 11/2004 | Fukushima et al. | |
| 6,890,968 B2 | 5/2005 | Angeletakis et al. | |
| 6,899,948 B2 | 5/2005 | Zhang et al. | |
| 7,074,042 B2 | 7/2006 | Allred et al. | |
| 7,081,485 B2 | 7/2006 | Suh et al. | |
| 7,192,280 B2 | 3/2007 | Allred et al. | |
| 7,632,098 B2 * | 12/2009 | Falsafi et al. | 433/215 |
| 7,649,029 B2 * | 1/2010 | Kolb et al. | 523/117 |
| 7,767,731 B2 * | 8/2010 | Chen et al. | 523/118 |
| 2003/0211051 A1 | 11/2003 | Majeti et al. | |
| 2004/0229973 A1 * | 11/2004 | Sang et al. | 523/118 |
| 2005/0089821 A1 | 4/2005 | Allred et al. | |
| 2006/0229380 A1 * | 10/2006 | Hare | 523/115 |
| 2007/0207445 A1 * | 9/2007 | Pitel | 433/224 |
| 2009/0011387 A1 * | 1/2009 | Sang et al. | 433/228.1 |

FOREIGN PATENT DOCUMENTS

| | | |
|---|---|---|
| CA | 2202732 | 10/1997 |
| CA | 2074128 | 4/1998 |
| DE | 19508586 | 9/1996 |
| WO | WO 01/30307 | 5/2001 |
| WO | WO 2004/105629 | 12/2004 |

* cited by examiner

*Primary Examiner* — Tae H Yoon
(74) *Attorney, Agent, or Firm* — David A. Zdurne; Douglas J. Hura; Leana Levin

(57) ABSTRACT

Dental compositions comprising a polymerizable compound, filler system of nanometer-sized silica particles, and polymerization system capable of being activated by light are provided. The compositions further contain a solvent such as a mixture of 1-butanol and acetone and may contain water. The nanometer-sized silica particles, having an average particle size of about 1 nm to about 100 nm, are uniformly dispersed within the resin. The compositions can be applied as a polish, sealant, bleach guard, or other coating material to the surfaces of dental restorations and teeth. Self-etching and non-self-etching compositions are provided. The cured coating forms a protective, durable film that enhances the shine and luster of the restorations and teeth.

5 Claims, No Drawings

DENTAL COMPOSITIONS FOR COATING RESTORATIONS AND TOOTH SURFACES

CROSS-REFERENCE TO RELATED APPLICATIONS

Related Applications

This patent application claims the benefit of and priority to U.S. Provisional Patent Application Ser. No. 60/928,766, filed on May 11, 2007, which is herein incorporated by reference for all purposes.

BACKGROUND OF THE INVENTION

1. Field of the Invention

The present invention relates generally to dental compositions containing polymerizable compounds and nanometer-sized filler particles. The dental compositions can be applied as a polishing, sealant, bleach guard or other coating to the surfaces of dental restorations and teeth. The composition is cured to provide a durable and smooth coating. This improves the luster and aesthetic appearance of the restorations and teeth.

2. Brief Description of the Related Art

Dental professionals use polishing compositions (or varnishes) to coat surfaces of dental restorations and natural teeth. By the term "dental restoration," as used herein, it is meant any material used to restore or replace lost tooth structure, teeth, or oral tissue including, but not limited to, fillings, inlays, onlays, veneers, crowns, and bridges.

For example, a dental practitioner may "fill a cavity" in a tooth with a composite filling material. Upon completing this step, the filling may have a relatively rough and uneven surface. So, the practitioner finishes the surface of the filling using high-speed dental burs. Then, the practitioner applies a polishing composition to the finished filling surface. The polishing composition provides a hard and smooth coating over the restoration. The finished restoration has a shiny and glossy appearance.

The dental industry is constantly looking to develop new polishes (or varnishes) that can be applied to the surfaces of restorations and teeth. For example, Pflug et al., U.S. Pat. Nos. 6,399,037 and 6,693,037 disclose dental materials including varnishes, sealants, and bonding agents containing nanoscale filler particles having a primary particle size of 1 to 100 nm. Suitable particles that can be used to prepare the nanoscale fillers are described as ground glass, ground quartz, highly dispersed silica, zeolite, laponite, kaolinite, vermiculite, mica, ceramic metal oxides, alumina, pyrogenic silica, sparingly volatile oxides of titanium, zirconium, germanium, tin, zinc, iron, chromium, vanadium, tantalum, and niobium. A sol of the filler particles in an organic solution is first prepared. The particles are treated with a silanizing agent so they can form a stable, low viscosity sol (about 1 Pas). After the particles have been dried, they are mixed with polymerizable monomers under high shear. The '037 patents describe the resulting dental material as having improved abrasion-resistance and surface-hardness. The dental material can be applied as a thin film.

Jia, U.S. Pat. No. 6,730,715 discloses curable dental compositions that can be used as cavity fillings, adhesives, sealants, luting agents, cements, orthodontic bonding materials, or restoratives. The composition includes acrylate and methacrylate monomers as well as a co-curable phosphoric acid ester. A curing system comprising polymerization initiators and accelerators is present in the amount of 0.01 to 5 weight percent. Water is added to the composition in the amount of 1 to 50 weight percent.

Stannard et al., U.S. Pat. No. 6,797,767 discloses polymerizable composite materials that can be used as restoratives, bonding agents, and adhesives. The material comprises at least one multifunctional acid containing monomer such as Bis-2(methacryloxy)ethyl phosphate; a non-reactive filler such as micron or submicron-sized particles of silica; a polymerization system capable of being activated by light to polymerize the composite material; and water. The composite material is applied to the tooth and then is set or cured by exposing the material to visible light.

Fukushima et al., U.S. Pat. No. 6,818,679 discloses a photopolymerizable dental composition that can be applied to the surface of crowns, fillings, and dentures. The composition comprises: a) a polyfunctional acrylate, b) a volatile (meth)acrylate compound, c) a fluoroalkyl group constituted of at least one fluorocarbon-containing (meth)acrylate compound, and d) an acyl phosphine oxide-based polymerization initiator. The composition is cured upon irradiation with visible light. The resulting cured coating is colorless and transparent with good durability, abrasion resistance and resistance to discoloration according to the '679 patent.

Zhang et al., U.S. Pat. No. 6,899,948 discloses dental materials comprising a hardenable resin and "nano-sized" silica particles dispersed within the resin. By "nano-sized," it is meant that the silica particles have an average diameter size of less than 200 nm. The nano-sized silica particles are further described as being discrete and non-agglomerated and in a dry powder form. The dental materials can be used as adhesives, crowns, fillings, cavity liners, cements, orthodontic devices, prostheses, and sealants according to the '948 patent.

Suh et al., U.S. Pat. No. 7,081,485 discloses a dental composition comprising a multiacrylate compound and a photo initiator that can be light-cured by a curing light or light box system. The multiacrylate compound comprises at least five acrylate functionalities per molecule; and the composition does not comprise methyl methacrylate. The photo initiator is present at a concentration of at least about 6 weight percent. The composition can further contain fillers, nanofillers, and glass particles. Upon curing, the composition forms a coating having a surface lacking an oxygen inhibition layer. The composition can be used as dental coatings and sealants.

Although some of the foregoing dental compositions are generally effective in improving the luster and aesthetic appearance of the restoration and tooth, they have drawbacks and there is a need for an improved dental polishing composition.

One disadvantage with traditional polishing compositions is that the surface of the tooth must be pre-etched before the composition can be applied thereto. The etching step is not only time consuming but certain patients also are very sensitive to the acid etchants used on the tooth surface. Therefore, dentists are looking for a one-step dental polish that will work for restorations and tooth enamel surfaces. Dentists would be interested in such a dental polish because it could be applied without first acid-etching the restoration or tooth surface.

Furthermore, some traditional dental polishes have poor stain-resistance. Discolorations and stains may form on the tooth surfaces due to ingestion of coffee, tea, soda, or other food and beverages. An improved polishing composition that can provide a protective and durable film coating having high stain-resistance is needed in the dental market. Compositions having high stain-resistance could be applied to bleached teeth to protect the whitened surfaces.

Another problem with conventional polishing compositions is their poor wear-resistance. As the coating of traditional polishing composition wears away, the underlying restoration may lose its shine and luster. This can lead to the restoration having a dull surface and non-aesthetic appearance. In such instances, the patient must make periodic dental office visits so the dental practitioner can polish the surface of the restoration and restore its shine. Polishing the restoration can be a relatively lengthy procedure requiring different dental instruments and polishing pastes. Eliminating this polishing step would be a benefit to both the patient and practitioner. Accordingly, there is a need for a polishing composition having wear-resistance that can be applied over dental restoration and tooth surfaces. The polish should be capable of providing a protective and durable coating having high scratch/abrasion resistance.

The present invention provides dental composition having the above described desirable properties as well as other benefits and advantages. These include, for example, 1) the capability of being cured by multiple light sources including light emitting diode (LED) and halogen curing lights, 2) low viscosity which makes it easier for a practitioner to apply the composition onto the targeted area, and 3) a less yellowish colored appearance so the composition does not change the color of the underlying substrate. The dental compositions of this invention can be applied as a polish, sealant, bleach guard or other coating material to the surfaces of dental restorations and teeth.

SUMMARY OF THE INVENTION

The present invention provides dental compositions used to coat dental restorations and tooth surfaces. For example, in one method of use, the composition is applied to the surfaces of bleached teeth. The composition forms a film coating that protects the whitened surfaces. One version of the composition is self-etching and comprises: a) about 10 to about 60 weight % polymerizable compound selected from the group consisting of urethane compounds and Bis-GMA compounds, and mixtures thereof; b) about 1 to about 40% by weight polymerizable acidic compound; c) about 3 to about 60% by weight silica particulate having an average particle size in the range of about 1 nm to about 100 nm; d) about 1 to about 30% by weight water; and e) about 10 to about 60% by weight solvent. Because this composition is considered to be self-etching, the tooth surface does not need to be acid-etched prior to application. The composition can be applied as a coating directly onto the restoration or tooth surface. Subsequently, a dental curing light can be used to cure and harden the coating.

In a second version, the surface of the tooth is acid-etched prior to applying the composition thereon. The composition is applied to the surface of the pre-etched tooth surface and cured using a light source. This composition comprises the following components: a) about 10 to about 60 weight % polymerizable compound selected from the group consisting of urethane compounds and Bis-GMA compounds, and mixtures thereof; b) about 0 to about 15% by weight polymerizable acidic compound; c) about 3 to about 60% by weight silica particulate having an average particle size in the range of about 1 nm to about 100 nm; and d) about 10 to about 60% by weight solvent.

DETAILED DESCRIPTION OF THE PREFERRED EMBODIMENTS

The present invention relates to dental compositions that can be applied as coatings to dental restorations and tooth surfaces. In general, the compositions comprises a polymerizable compound, silica particulate, and photopolymerization system as discussed in further detail below.

In one embodiment, the composition is considered to be "self-etching." By the term, "self-etching," as used herein, it is meant the substrate does not need to be acid-etched prior to applying the composition thereto. When self-etching compositions are used in accordance with this invention, a high strength bond is formed between the composition and substrate (restoration or tooth surface.) Because the composition etches, primes, and bonds to the restoration or tooth surface in a single step, overall patient treatment efficiency is improved. The dental practitioner does not need to spend time acid-etching the restoration or tooth surface, and the patient spends less time in the dental chair. Furthermore, there tends to be less post-treatment tooth sensitivity, because there are no acid-etching steps. In a second embodiment, the composition is considered to be "non-self-etching." By the term, "non-self-etching," as used herein, it is meant the substrate needs to be acid-etched prior to applying the composition thereto. For non-self-etching compositions, the restoration or tooth surface is first cleaned. A liquid or gel acid etchant is applied to onto the restoration or tooth surface to prepare it. Then, the tooth is rinsed and dried. The composition is applied to the surface of the pre-etched restoration or tooth surface and cured using a visible light source. The resulting hardened film coating strongly adheres to the restoration or tooth surface. The coating is durable and has good wear-resistance.

Polymerizable Compounds

The polymerizable compounds used in the compositions are capable of being cured or hardened to form a polymer network. The composition contains at least one polymerizable compound having at least one free-radically active functional group. Such polymerizable compounds include, for example, monomers and oligomers containing at least one ethylenically unsaturated bond that is capable of undergoing addition polymerization. Such free radically polymerizable compounds include, but are not limited to, mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, tetraethylene glycol di(meth)acrylate, 1,3-propanediol diacrylate, 1,3-propanediol dimethacrylate, trimethylolpropane tri(meth)acrylate, 1,2,4-butanetriol trimethacrylate, 1,4-cyclohexanediol diacrylate, 1,6-hexanediol di(meth)acrylate, pentaerythritol triacrylate, pentaerythritol tetraacrylate, pentaerythritol tetramethacrylate, sorbitol hexacrylate, 2,2-bis [4-(2-hydroxy-3-acryloyloxypropoxy)phenyl]propane; 2,2-bis[4-(2-hydroxy-3-methacryloyloxypropoxy)phenyl] propane (Bis-GMA); 2,2-bis[4-(acryloyloxy-ethoxy)phenyl] propane; 2,2-bis[4-(methacryloyloxy-ethoxy)phenyl] propane (or ethoxylated bisphenol A-dimethacrylate) (EBPADMA); urethane di(meth)acrylate (UDMA), diurethane dimethacrylate (DUDMA); polyurethane dimethacrylate (PUDMA); alkoxylated pentacrythritol tetraacrylatel; polycarbonate dimethacrylate (PCDMA); the bis-acrylates and bis-methacrylates of polyethylene glycols; copolymerizable mixtures of acrylated monomers; acrylated oligomers; acidic monomers such as dipentaerythritol pentacrylate phosphoric acid ester (PENTA); and bis[2-(methacryloxyloxy)-ethyl]phosphate; and compounds including at least one carboxylic acid group such as acrylic or methacrylic acid. Mixtures of the above-described polymerizable compounds can be used. Preferably, the polymerizable compound is selected from the group consisting of urethane compounds and Bis-GMA compounds and mixtures thereof. The polymerizable compounds are typically present in the composition in an amount in the range of about 10% to about 60% by weight and more preferably in the range of 20% to 50%.

The compositions further contain a polymerizable acidic compound to improve adhesive and bonding properties. Such compositions can more effectively bond to restoratives and tooth surfaces. For example, the composition may contain organic esters of one or more phosphoric acids or sulfuric acids, wherein the organic portion of the ester contains at least one polymerizable ethylenically unsaturated group. Examples of unsaturated phosphorus containing acid esters which may be used include, but are not limited to, monomers containing phosphoric acid groups such as hydroxyethyl methacrylate monophosphate, 2,2,-bis(.alpha.-meth-acryloxy-.beta.-hydroxy-propoxyphenyl)propane diphosphonate (BIS-GMA diphosphonate), BIS-GMA diphosphate, methacryloxyethyl phosphate, glyceryl dimethacrylate phosphate, and dipentaerythritol pentacrylate phosphoric acid ester (PENTA). In the self-etching version, the polymerizable acidic compound is preferably present in an amount in the range of about 1% to about 40% by weight and more preferably in the range of 10% to 30%. In the non-self-etching version, the polymerizable acidic compound is optional. Preferably, the acidic compound is present in an amount in the range of about 0.1% to about 15% by weight and more preferably in the range of 0.25 to 10%.

The compositions may contain a polymerizable compound having at least one free-radically active functional group as described above in addition to the polymerizable acidic monomer. The polymerizable acidic compound contains at least one group that is co-curable with the free-radically active functional group of the polymerizable compound as described above. For example, the composition may contain a mixture of acrylic acid and PENTA. Adding acrylic acid helps improve bonding of the composition to the restoration or tooth surface. The acrylic acid is preferably added in an amount of about 0.1 to about 3.0 weight percent to improve adhesion strength and help maintain viscosity. Such compositions form a high strength bond to tooth enamel and dentin, but they are not considered self-etching materials. Thus, it is recommended that the surface of the tooth first be prepared by applying a liquid or gel etchant. For example, phosphoric acid can be used to etch the surface of the tooth. The acid-etched tooth is rinsed and dried. Then, the composition containing acrylic acid and PENTA can be applied.

Solvents

One problem with using the above-described polymerizable compounds in dental compositions is they tend to have high viscosity and may not flow easily from a bottle or other container. It is important that the composition be thick enough to provide a durable protective film coating over the surface of the restoration or tooth. At the same time, the dental practitioner must be able to work with and handle the composition. Therefore, the viscosity of the composition must be sufficiently low so that it can be easily ejected from the bottle or other container. Adding a solvent to the composition helps reduce viscosity and makes it easier for the practitioner to apply the composition to the targeted area. Examples of suitable solvents include, but are not limited to, acetone, 1-butanol, pentane, hexane, octane, methyl pentane, dimethyl pentane, trimethyl pentane, methyl hexane, dimethyl hexane, methyl butane, dimethyl butane, trimethyl butane, cyclohexane, cycloheptane, mineral spirits, ethyl acetate, propyl acetate, ethers, methylene chloride, chloroform, cyclohexanone, heptane, methyl acetate, methyl ethyl ketone, methyl propyl ketone, and tetrahydrofuran, and the like. Mixtures of solvents can be used in the composition. Preferably, the composition of this invention contains acetone solvent in an amount in the range of about 1 to about 60 weight percent and 1-butanol in an amount in the range of about 1 to about 25 weight percent based on weight of the composition. A mixture of high boiling point butanol solvent and low boiling point acetone solvent is preferred because it optimizes the evaporation rate and effectively lowers the viscosity of the composition.

The self-etching composition further contains water. Adding water to the composition is advantageous, because it works to dissociate the acid or monomer with acidic functional groups (for example, PENTA) in the composition. The dissociated acidic groups then demineralize the underlying intact tooth substrate and thus strong bonding can form between the composition and tooth surface. Water is also a good solvent for adjusting the evaporation rate of the composition. In general, water can be added to the composition in an amount in the range of about 1% to about 30% by weight and preferably it is present in an amount of 10% to 20%.

Filler System

In addition to the polymerizable compounds described above, the compositions of this invention contain nanometer-sized silica particles having an average diameter size in the range of about 1 nm to about 100 nm. To make discrete silica particles having this average diameter size, agglomerates and aggregates of the particles need to be broken down. This process is referred to as milling or grinding the particles, and various media mills can be used to destroy particle clusters and produce individual particles having this average diameter size. The particles can be prepared by media milling in apparatus including, but not limited to, attritor, agitator, and vibratory mills. The milling action breaks down particle clusters and reduces the size of individual particles. Of course, some particle clusters will not be fully broken down, and there may be some agglomerated or aggregated particles having an average diameter size in the range of about 1 nm to about 600 nm remaining that can be used in the filler system.

The silica particles may be dispersed within a polymerizable urethane resin to form a filler system, and then this filler system can be added to the formulation. The silica particles may be surface treated with a silane compound or other coupling agent so that they can be more uniformly dispersed within the resin. Suitable silane compounds include, but are not limited to, gamma-methacryloxypropyltrimethoxysilane, gamma-mercaptopropyltriethoxysilane, gamma-aminopropyltrimethoxysilane, and combinations thereof. Surface treating the silica particles with the silane compound helps make the particles less likely to agglomerate in the dispersion. The surface-treated particles are therefore distributed more homogenously within the resin matrix.

A sol of the silica particles in non-aqueous solution can be prepared by silanizing the particles with a silane compound in a solvent such as acetone. Other solvents such as 1-butanol, pentane, hexane, octane, ethanol and the like can be used. The silica particles can be mixed with the silane compound with or without the presence of acetone solvent. The mixture can be placed on a roller at a speed of 60 revolutions per minute for 60 minutes at 20° C. or above. Once the silica particles have been surface-treated, that is, silanized, they are ready to be added to the urethane resin.

The polymerizable urethane resin is preferably prepared by reacting 2,2-bis[4-(2-hydroxy-3-methacryloyloxypropoxy)phenyl]propane (Bis-GMA) and hexamethylene diisocyanate (HMDI). The reaction is carried out in a double planetary mixer. Nanometer-sized surface-modified fumed silica particles and other fillers, if desired, are added to the resin solution in the attritor mill. For example, glass beads can be added to the resin solution. It is important that the mixture in the attritor mill have the proper viscosity. If the viscosity of the mixture is too high, the shearing forces in the mill will not be sufficient to prepare a homogeneous dispersion of particles. On the other hand, if the viscosity of the mixture is too low, there will not be sufficient particle contact and grinding, and the silica particle agglomerates and aggregates will not be broken down sufficiently.

The dental compositions of this invention may further contain conventional inorganic fillers in addition to the above-described nanometer-sized silica particles. Examples of conventional fillers include glass, quartz, barium borosilicate, strontium borosilicate, borosilicate, barium silicate, strontium silicate, lithium silicate, lithium alumina silicate, calcium phosphate, alumina, zirconia, tin oxide, titanium dioxide, and the like. Such conventional fillers typically have a particle size in the range from about 0.1 to about 5.0 microns and are silane-treated. In this manner, the total filler content can be increased and this may further enhance the strength and other mechanical properties of the composition. The total amount of filler particles in the composition is typically in the range of about 3% to about 60% based on the total weight of the composition and preferably in the range of about 5% to about 20%.

Photopolymerization System

The compositions further include a photopolymerization system capable of being activated by visible light having a wavelength in the range of about 400 to about 550 nm. The photopolymerization system includes a photoinitiator for example, benzophenone, benzoin and their derivatives or alpha-diketones and their derivatives. A particularly preferred photoinitiator is camphorquinone (CQ) compound. Preferably, photopolymerization is initiated by irradiating the composition with blue, visible light preferably having a wavelength in the range of about 420 to about 530 nm. A standard dental light-curing source can be used to irradiate the composition as discussed further below. The camphorquinone (CQ) compounds have a light absorbency range of about 420 to about 500 nm and generate free radicals for polymerization when irradiated with light having a wavelength in this range.

The polymerization photoinitiator is preferably present in the composition in the range of about 0.05 to about 1.00 wt. % and more preferably in the range of about 0.10 to about 0.25 wt. % based on weight of the composition. One advantage of the composition this invention is that it contains only a small amount of CQ compound. Using such a small amount of CQ, which has a slightly yellowish color, prevents discoloration of the composition. By contrast, compositions containing a high concentration of CQ are more likely to be yellow.

The photopolymerization system further includes a polymerization accelerator, which is preferably a tertiary amine. One example of a suitable tertiary amine is ethyl 4-(dimethylamino)benzoate (EDAB). The polymerization accelerator is preferably present in the composition in the range of about 0.10 to about 2.00 wt. %, and more preferably in the range of about 0.1 to about 0.5 wt. %, based on weight of the composition. Other tertiary amines may be used such as, for example, triethanol amine, N,N,3,5,N,3,5-tetramethyl aniline, 4-(dimethylamino)-phenethyl alcohol, dimethyl aminobenzoic acid ester, dimethyl-p-toluidine, dihydroxyethyl-p-toluidine, hydroxyethyl-p-toluidine, and the like.

In addition, the photopolymerization system may include a polymerization inhibitor such as, butylated hydroxytoluene (BHT); hydroquinone; hydroquinone monomethyl ether; benzoquinone; chloranil; phenol; butyl hydroxyanaline (BHA); tertiary butyl hydroquinone (TBHQ); tocopherol (Vitamin E); and the like. The polymerization inhibitors act as scavengers to trap free radicals in the resulting composition and to extend the shelf stability of the composition. The polymerization inhibitors are typically present in the composition in the range of about 0.01 to about 2 wt. % based on weight of the composition. The composition may include one or more polymerization inhibitors.

Additives

The compositions also can include additives to provide specially desired properties. For example, fluoride-releasing agents; flavorants; pigments; fluorescent agents; opalescent agents; ultra-violet stabilizers; anti-oxidants; surfactants, adhesion promoters, viscosity modifiers, and the like can be added. The composition preferably contains about 0.5 to about 3.0 weight percent of a surfactant (leveling agent) to improve the wetting action of the composition. Examples of suitable leveling agents include polysiloxane-based materials such as Ciba EFCA 3000 (Ciba Geigy); organic-modified polysiloxane based materials such as Borchi® Gol LA2; and polyacrylate based materials such as BYK-350 surfactants available from BYK Chemie.

The self-etching and non-self-etching dental compositions of this invention may be applied to the restoration or tooth surface using techniques known in the art. First, the surface of the restoration or tooth is cleaned thoroughly. Prophylaxis pastes can be used to clean the surface. If a non-self-etching composition is used, the surface is acid-etched after the cleaning step to further enhance the adhesion between the coating and tooth surface. The etched surface is rinsed with water. Next, the surface is dried with cotton rolls, air syringe, or other appropriate materials. The material is applied to the surface with a microbrush or other suitable applicator.

In one form of the invention, the material can be provided as a dental polish. The polish is provided as an acetone-like material in a bottle or in unit dose packaging. The polish can be applied onto composite restorations such as fillings. A generous amount of the polishing composition is applied onto the restorative material and all conditioned enamel surfaces. That is, the polish is painted onto the surface to provide a film coating. Next, the coating is air dried using a gentle air stream for about ten (10) seconds. The coating is finally cured by visible light irradiation. Standard dental curing lights may be used to cure the composition. Suitable Light-Emitting Diode (LED) dental curing lights include, for example, those sold under the brand names: SmartLite iQ2™ and SmartLite PS™ (Dentsply); Elipar® (3M Espe); and L.E. Demetron II™ (Kerr). Alternatively, halogen lights, which have a broad spectral light output can be used to cure the coating. Once cured, the material provides a smooth and durable film coating over the restoration. The polished restoration has a shiny and glossy appearance.

One advantage of the composition of this invention is that it can be activated by LED or halogen dental curing lights. Camphorquinone (CQ)/ethyl 4-(dimethylamino)benzoate (EDAB) photoinitiators generally require light having a wavelength of about 420 to about 500 nm to be activated as discussed above. LED lights normally emit light in the wavelength spectrum of about 450 nm to 480 nm, while halogen lights emit light having a wavelength in the range of about 390 to 500 nm.

Because the compositions contain PENTA or other suitable acidic monomer, they have good adhesion to the restoration and tooth. In one version, the materials are used as sealants applied over tooth surfaces to seal pits and fissures. Such sealants are applied to the surface of a tooth in order to provide long-term protection against dental caries caused by the accumulation of bacteria. The bacteria in plaque produce acids that eat into the tooth, eventually causing cavities to form therein. Pits and fissures may develop in the surface of a tooth, and bacteria tend to accumulate in these areas. Sealants are commonly used to fill the pits and fissures in the surface of a tooth. The adhesive-promoting composition of this invention can be used as pit and fissure sealants. Once applied and cured, the sealants provide a smooth and durable seal preventing the ingress of fluids, food, and debris. The cured sealants have a glossy surface finish. The compositions can be used as sealants over composite restorations to prevent composite material from micro-leaking at the margins and contacts between the restoration and tooth. The compositions provide an adhesive seal against micro-leakage of composite material so that the margins of the restoration are well protected.

Furthermore, the self-etching compositions of this invention can be applied onto the surfaces of bleached teeth. The polishing composition forms a protective film coating that protects the bleached tooth surfaces from discolorations and stains caused by food and beverages. In this manner, the composition functions as a "bleach guard" protecting the whitened surfaces from harmful agents. Furthermore, the protective coating may reduce the number of bleaching steps that normally must be performed to on the patient's teeth to maintain aesthetics and appearance. This would be particularly beneficial to patients who need to undergo multiple bleaching steps but are sensitive to bleaching agents.

The invention is further illustrated by the following Examples using the below-described test methods, but these Examples should not be construed as limiting the scope of the invention.

Test Methods

Adhesion Strength

1. Bonding to Enamel:

Conditioning

Immerse extracted human or bovine molars in water at 4° C. for 24 hrs prior to use. Sand the enamel using wet 320 grit abrasive paper and then 600 grit abrasive paper under running water.

Sample Preparation

Prepare a minimum of 5 teeth for each material/variable to be tested. Apply the polish to enamel and light cure in accordance with the manufacturer's directions for use (DFU). Fill gelatin capsule post (4.5 mm in diameter) with the composite resin, TPH Spectrum (Dentsply) and then position onto the polish coated surface area. Remove the excess flashing from the capsule posts using a dental explorer and light-cure the resin-containing posts with a SmartLite iQ2 LED dental curing light (Dentsply) at 550 mW/cm$^2$ intensity for 20 seconds three times around the post to adhere the posts to the polish coated surface. Place the substrate samples with bonded gelatin posts in a distilled water bath at 37° C. for 24 hours before testing for shear bond strength.

Shear Bond Strength Testing

Determine the shear bond strength using an Instron Model 4400 electromechanical testing unit (with a crosshead speed of 1 mm/min).

2. Bonding to Composites:

Bonding to composites is similar to bonding to enamel except for substrate preparation. A composite dental restorative material coated with the polish is filled into a mold measuring 20 mm×10 mm×5 (height) and cured with a TRIAD 2000 visible light-curing unit (Dentsply) for two minutes on each side. Then, the surfaces of composite substrates are sanded with 600 grit abrasive paper and gently dried.

Color of Coating

Color measurements were made on the non-coated (standard) surface of a restoration and on the coated surface of restoration. The measurements were made with a Macbeth® 2020 Colormeter (Gretag Macbeth). The color differences between the two surfaces were calculated using the CIE L*a*b* system. The CIE ΔE values were calculated according to the following formula:

$$\Delta E = [(L^*_1 - L^*_2)^2 + (a^*_1 - a^*_2)^2 + (b^*_1 - b^*_2)^2]^{1/2}$$

Where:

$L^*_1$, $a^*_1$, and $b^*_1$ is the colorimetric value of standard surface, and $L^*_2$, $a^*_2$, and $b^*_2$ is the colorimetric value of coated surface.

1. Preparation of Standard:

A composite dental restorative material (Esthet Flow B1) was filled into a mold measuring 20 mm (diameter)×2 mm (thickness) and cured in a TRIAD 2000 visible light curing unit (Dentsply) for two minutes on each side. Then the surfaces of composite substrates were wet-sanded with 600 grit abrasive paper and gently dried.

2. Preparation of Sample:

A composite dental restorative material (Esthet Flow B1) was filled into a mold measuring 20 mm (diameter)×2 mm (thickness) and cured with a TRIAD 2000 visible light curing unit (Dentsply) for two minutes on each side. Then, the surfaces of composite substrates were wet-sanded with 600 grit abrasive paper and gently dried. The polish was coated on the sanded side of sample and cured in the TRIAD 2000 visible light curing unit for 2 minutes.

Coffee Stain-Resistance

The same procedures used to prepare the samples and standards for measuring the color of the dental coating (as described above) were followed to prepare the samples and standards for measuring stain-resistance. Coated samples were immersed in dark coffee solution for twenty-four (24) hours before testing. The ΔE between standard and the coated surfaces was measured using a Macbeth® 2020 Colormeter (Gretag Macbeth).

Tooth Brushing Wear-Resistance

A tooth brushing machine was used to evaluate the wear-resistance of the coating. The machine conforms to ISO/TS 14569-1. The coating surface was tested under a brush with reciprocating movement.

1. Preparation of Sample:

A composite dental restorative material (Esthet Flow B1) was first placed in a mold measuring diameter 20 mm×10 mm×5 mm (height) and cured with a TRIAD 2000 visible light curing unit (Dentsply) for two minutes on each side. Then, the surfaces of composite substrates were wet sanded with 600 grit abrasive paper and gently dried. The polish was coated on the sanded side of sample and cured according to direction for use by the manufacturer. The coating surface was then tested in the tooth brushing machine. The load that pressed the brush against the coating surface was 1.4N and temperature of the toothpaste slurry was kept at 23±3° C. The abrasive slurry was prepared from a mixture of toothpaste and deionized water in the ratio of 2 g of water to 1 g of toothpaste.

2. Measuring of Brushing Time:

The surface gloss of the coating was measured initially after three (3) minutes and then every sixty (60) minutes up to a maximum of three-hundred and sixty (360) minutes using a Novo Curve Small Area Glossmeter. The total brushing time was recorded at the point when the surface gloss of the coating decreased to a value of less than 10 at a 60° angle. After 360 minutes of toothbrushing time, if the surface gloss did not decrease to ten (10) or less, a time of 360 minutes was recorded.

EXAMPLES

Chemical compounds used in the following examples are listed in Table A below.

TABLE A

Chemical Compounds

| Abbreviation | Material List | Manufacturer |
|---|---|---|
| BisGMA | 2,2' bis[p-(2'-hyroxy-3' methacry (oxypropoxy)phenyl]propane | Cook Composite & Polymer |
| HMDI | Hexamethylene diisocyanate | Bayer |
| BHT | Butylated Hydroxy Toluene | PMC Specialty Inc |
| T-9 | Dabco T-9 Catalyst | Alderich Chemical Inc. |
| Nanofiller | Nanometer-sized modified fumed silica | Dentsply DeTrey |
| PENTA | Dipentaerythritol Penta Acrylate Phosphate | Dentsply (Caulk) |
| BYK 350 | Polyacrylate | BYK Chemie |
| CQ | Camphorquinone | Hampford Research |
| EDAB | Ethyl 4-dimethylamino Benzoate | Dentsply (Caulk) |

Material 1 (Polymerizable Modified Urethane Resin—Precursor to Material 2)

A Ross mixer (Model LDM-1, Charles Ross and Son Company) equipped with a water jacket and two agitators was charged with a mixture of 1000 grams of Bis-GMA, 130 grams of HMDI, 0.57 grams of BHT and 0.57 grams of T-9. The water jacket temperature was increased to 50° C. through Mokon 15 temperature control system. The mixture was agitated at a velocity of 120 rpm in the first two hours and then decreased to 60 rpm for another 2 hours.

The free NCO content (as measured according to the procedures below) was determined at the end of reaction. The reaction time was extended if the free NCO content was greater than 0.1%.

Determination of Free Isocynate Content:

Weigh 0.250 gram±0.001 gm of sample into a 250 mL Erlenmeyer flask on an analytical balance. Add 25 mL of toluene by graduate, and stopper with aluminum foil wrapped corks, then mix on stir plate until sample is in solution. Pipet 25 mL of 0.1N n-butylamine solution and stir for a few minutes. While stirring, add 100 mL of isopropyl alcohol and five drops of bromophenol blue indicator solution. Titrate with 0.1N hydrochloric acid solution to a yellow-green end point. Run a blank including all reagents but omitting the sample.

$$\text{Free Isocynate content} = \{(B-V) * N * 4.202\}/W$$

Where:
B=mL of 0.1N HCl for blank
V=mL of 0.1N HCl for sample
N=Normality of HCL solution
W=Weight of sample (gm)

Specification of Material 1
Viscosity: 300-800 Pa s/50° C.
Free isocynate content: <less than 0.1%

Material 2 (Polymerizable Modified Urethane Resin Solution—Precursor to Material 3)

Material 2 was prepared by mixing the following ingredients for 2 hours at 40° C.

| | |
|---|---|
| Material 1 (as described above) | 86 parts |
| Acetone | 14 parts |

Material 3 (Polymerizable Modified Urethane Resin Solution Containing Nanometer-Sized Fumed Silica Particles Dispersed Therein)

Material 3 was prepared by grinding the following ingredients for 60 minutes at room temperature in a Szegvavi attritor mill (01 HD, Union Process, Inc.).

| | |
|---|---|
| Material 2 (as described above) | 325 parts |
| Acetone | 218 parts |
| Nanometer-sized fumed silica particles | 56 parts |
| Glass beads (φ 3 mm) | 1002 parts |

Example 1

A polishing composition with high stain and wear resistance was prepared from the components described below in Table 1. This composition contains a relatively small amount of adhesion promoter. Before applying this composition, the tooth or restoration surface should be pre-etched.

TABLE 1

High Stain and Wear Resistance Composition

| Components | Weight Percentage |
|---|---|
| Dipentaerythritol Penta Acrylate Phosphate | 0.25% |
| Material 3 | 75% |
| BYK 350 (50% in Acetone) | 1% |
| 1-Butanol | 4.9% |
| Acrylic Acid | 1.0% |
| Acetone | 17.45% |
| Camphorquinone | 0.1% |
| Ethyl 4-dimethylamino Benzoate | 0.3% |

The composition of Example 1 was tested for various physical and chemical properties in accordance with the above test methods and the results are reported below in Table 3.

Example 2

A polishing composition with self-etching properties was prepared from the components described below in Table 2. This composition is considered to be self-etching. The tooth surface does not need to be acid-etched before applying this composition.

TABLE 2

Self-Etching Composition

| Components | Weight Percentage |
|---|---|
| Dipentaerythritol Penta Acrylate Phosphate | 15.4% |
| Material 3 | 35.1% |
| BYK 350 (50% in Acetone) | 0.9% |
| 1-Butanol | 8.5% |
| Acrylic Acid | 0.9% |
| Acetone | 28.9% |

TABLE 2-continued

Self-Etching Composition

| Components | Weight Percentage |
|---|---|
| Camphorquinone | 0.09% |
| Ethyl 4-dimethylamino Benzoate | 0.27% |
| Deionized Water | 10% |

The composition was tested for various physical and chemical properties in accordance with the above test methods and the results are reported below in Table 3.

Comparative Example A

A commercially-available dental sealant, BISCOVER, from Bisco, Inc. was tested for various physical and chemical properties in accordance with the above test methods and the results are reported below in Table 3.

Comparative Example B

A commercially-available dental sealant, OPTIGUARD, from Kerr Manufacturing (Sybron Dental Specialties, Inc.) was tested for various physical and chemical properties in accordance with the above test methods and the results are reported below in Table 3.

Comparative Example C

A commercially-available dental sealant, GLOSS N SEAL, from Den-Mat Co. was tested for various physical and chemical properties in accordance with the above test methods and the results are reported below in Table 3.

Comparative Example D

A commercially-available dental sealant, SEAL-N-SHINE, from Pulpdent Corp. was tested for various physical and chemical properties in accordance with the above test methods and the results are reported below in Table 3.

Examples, but it also shows the highest stain-resistance to coffee. It is believed that the relatively high wear-resistance is due to the addition of nanometer-sized silica particles which were uniformly distributed in the resin. The material in Example 1 also shows better coffee stain-resistance than each of the comparative materials.

In general, it is difficult for the human eye to distinguish the color tone difference between respective materials if the $\Delta E$ value between the materials is less than 2. It is also believed that the relatively high stain-resistance of the material in Example 1 was due, at least in part, by the unique polymerizable modified hydrophobic urethane resin used in the material. The hydrophobic surface prevents the adsorption/deposition of water-soluble, acidic colored substances in coffee. This staining mechanism theory is supported by the material in Example 2 and its relative low stain-resistance properties. The material in Example 2 has a less hydrophobic surface, and it showed relatively less stain-resistance.

Enamel Shear Bond Strength

The self-etching polishing material in Example 2 shows an equal or greater enamel shear bond strength than the material in Example 1 and material in Examples A, B, C and D (which require a pre-etched step on enamel surface before application.). Enamel shear bond strength is a critical property for polishing compositions. If a coating layer debonds or drifts away from the tooth surface partially or completely, it will lose its aesthetic appearance. In general, bond strength above 15 Mpa is considered good bonding and bond strength above 20 Mpa is considered strong bonding similar to an adhesive. It was found that that the self-etching composition in Example 2 was a strong bonding material having a shear bond strength of 27.2 Mpa.

Change in Color

In addition, the materials in Examples 1 and 2 have the lowest $\Delta E$ values showing the difference in color between the between uncoated (standard) and coated surfaces. It is believed this is due to the low concentration of camphorquinone (0.1%) as the photo-initiator in the formulations. The polymerizable modified urethane resin (Material 1)

TABLE 3

| Physical and Chemical Properties | Example A Biscover | Example B Optiguard | Example C Gloss N Seal | Example D Seal n Shine | Example 1 | Example 2 |
|---|---|---|---|---|---|---|
| Shear Bond Strength to enamel (Mpa) | 27.4 | 17.2 | 23.7 | 18.9 | 28.3 | 27.2 |
| Shear Bond Strength to composite (Dyract Extra, Dentsply) (Mpa) | 19.3 | 16.8 | 16.8 | 26.6 | 21.4 | 22.1 |
| Wear Resistance (Time of Toothbrushing for Retaining Surface Gloss) | 3 minutes | 3 minutes | 3 minutes | 3 minutes | 360 minutes | 60 minutes |
| Color of Coating ($\Delta E$) | 2.2 | 1.0 | 1.3 | 2.0 | 0.8 | 0.8 |
| Coffee Stain-Resistance ($\Delta E$) | 11.8 | 8.4 | 3.0 | 3.0 | 2.0 | 5.3 |
| Viscosity at 25° C. (cp) | 650 | 400 | — | 1230 | 9-10 | 6-7 cp |

Various physical and chemical properties for the materials Comparative Examples A, B, C, D and Examples 1 and 2 are described in Table 3.

Wear-Resistance and Coffee Stain-Resistance

The material in above Example 1, not only has a higher wear-resistance than each of the materials in the Comparative makes it possible to use the low concentration of camphorquinine. Also, the materials in Examples 1 and 2 have lower viscosity than any of the materials in the comparative examples. The low viscosity of the material makes it easier for a practitioner to apply the composition to the targeted area.

As described above, the self-etching composition of the present invention does not require a pre-etching step, and it has a shear bond strength equal to that of traditional compositions. The self-etching composition is superior to all comparative examples in wear-resistance, and color of coating. Meanwhile, a non-self-etching composition of the present invention possesses a higher stain and wear resistance than all comparatives examples. As a result, the materials of the present invention can be used in different dental applications such as a polishing or sealant composition for dental restorations and teeth. The materials provide additional durability, stain-resistance and simplicity in handling.

Workers skilled in the art will appreciate that various modifications can be made to the illustrated embodiments and description herein without departing from the spirit and scope of the present invention. It is intended that all such modifications within the spirit and scope of the present invention be covered by the appended claims.

What is claimed is:

1. A non-self-etching dental composition, comprising:
   a. about 0.25 to about 10% by weight polymerizable acidic compound, the polymerizable acidic compound including a mixture of at least one unsaturated phosphorus containing acid ester comprising dipentaerythritol penta acrylate phosphate (PENTA) and an different unsaturated carboxylic acid monomer;
   b. a filler dispersion including a mixture having:
      (i) a polymerizable compound of about 10 to about 60% by weight of the dental composition, the polymerizable compound is prepared by reacting 2,2-bis[4-(2-hydroxy-3-methacryloyloxypropoxy)phenyl]propane (Bis-GMA) and hexamethylene diisocyanate (HMDI); and
      (ii) a silica particulate filler of about 3 to about 60% by weight of the dental composition, said silica particulate being dispersed in the polymerizable compound;
      (iii) wherein the mixture has an average particle size in the range of about 1 nm to about 100 nm;
   c. about 10 to about 60% by weight solvent; and
   d. a photopolymerization system capable of being activated by light, the photopolymerization system comprising a photoactive agent selected from the group consisting of camphorquinone; 2,4,6 trimethylbenzoyldiphenyl phosphine oxide; and ethyl (4-N,N-dimethylamino)benzoate.

2. The dental composition of claim 1, wherein the solvent comprises a mixture of 1-butanol and acetone solvents.

3. A method of applying a non-self-etching dental composition to a tooth surface or dental restoration, comprising the steps of:
   a) providing the composition of claim 1;
   b) acid-etching the surface of the tooth or dental restoration;
   c) applying the composition to the acid-etched surface of the tooth or dental restoration; and
   d) irradiating the composition with light so that the composition cures and hardens.

4. The method of claim 3, wherein the composition is cured by blue visible light having a wavelength in the range of about 400 nm to about 500 nm.

5. The dental composition of claim 1, wherein the different unsaturated carboxylic acid monomer is acrylic acid that is present in an amount of about 0.1 to about 3% by weight based on the total dental composition.

* * * * *